United States Patent
Faengewisch et al.

(10) Patent No.: US 6,897,325 B2
(45) Date of Patent: May 24, 2005

(54) METHOD OF PRODUCING BRANCHED FATTY SUBSTANCES

(75) Inventors: Christian Faengewisch, Dortmund (DE); Arno Behr, Dortmund (DE)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 0 days.

(21) Appl. No.: 10/250,590

(22) PCT Filed: Jan. 3, 2002

(86) PCT No.: PCT/EP02/00015
§ 371 (c)(1),
(2), (4) Date: Jul. 11, 2003

(87) PCT Pub. No.: WO02/055474
PCT Pub. Date: Jul. 18, 2002

(65) Prior Publication Data
US 2004/0054205 A1 Mar. 18, 2004

(30) Foreign Application Priority Data
Jan. 11, 2001 (DE) ........................ 101 00 893

(51) Int. Cl.[7] .................................. C09F 7/06
(52) U.S. Cl. .......................... 554/25; 554/26
(58) Field of Search ..................... 554/25, 26

(56) References Cited

U.S. PATENT DOCUMENTS

| 5,401,865 A | 3/1995 | Laufenberg et al. |
| 5,434,282 A | 7/1995 | Stern et al. |
| 6,153,772 A | 11/2000 | Hillion et al. |
| 6,452,029 B1 | 9/2002 | Hillion et al. |

FOREIGN PATENT DOCUMENTS

| EP | 0 511 982 B1 | 11/1992 | |
| EP | 0 621 257 A1 | 10/1994 | |
| EP | 0 894 785 A1 | 3/1999 | |
| EP | 0 976 715 A1 | 2/2000 | |
| EP | 0976715 A * | 2/2000 | |
| WO | WO 91/11425 A1 | 8/1991 | |
| WO | WO 9111425 A * | 8/1991 | ......... C07C/51/353 |

OTHER PUBLICATIONS

Behr et al, Fett Wissenschaft Tech.—Fat Science Tech, pp. 20–24, 1991.*

A. Behr, A. Laufenberg: "Synthese neuer versweigter Fettsäureester durch homogene Rhodiumkatalyse" Fett Wissenschaft Technologie–Fat Science Technology., vol. 93, No. 1, 1991, pp. 20–24, XP002198206 Conradin Industrieverlag. Leinfelden Echterdingen., DE ISSN: 0931–5985.

Gronowitz et al., "On the Syntheses of Branched Saturated Fatty Acids ", Lipids, vol. 28, No. 10, (1993), pp. 889–897.

Kinsman, Fatty Acids in Indusrty, Chapter 11, Marcel Dekker, Inc., New York, (1989), pp. 233–376.

* cited by examiner

*Primary Examiner*—Deborah D. Carr
(74) *Attorney, Agent, or Firm*—Aaron R. Ettelman

(57) ABSTRACT

Branched fatty compounds are made by a process which comprises reacting an unsaturated fatty compound and an α-olefin in the presence of a transition metal catalyst and a solvent mixture wherein the solvent mixture is a single liquid phase above 20° C. and is two liquid phases below 20° C.

13 Claims, No Drawings

METHOD OF PRODUCING BRANCHED FATTY SUBSTANCES

BACKGROUND OF THE INVENTION

This invention relates generally to oleochemical raw materials and, more particularly, to a new process for the homogeneously chemical oligomerization of unsaturated fatty compounds with olefins.

The derivatization of renewable raw materials, more particularly fats and oils, leads to economically and industrially interesting products such as, for example, plasticizers, lubricants and the like. In this connection, the use of homogeneously soluble transition metal compounds as catalysts has proved successful because high selectivities can be obtained with such catalysts, even under mild reaction conditions.

Interesting products include internally alkyl-branched fatty acid derivatives whose outstanding physical properties (for example low melting point, high chemical stability, low viscosity) make them potentially suitable for a number of applications [cf. S. Gronowitz et al. Lipids, 28,889 (1993) or D. V. Kinsman in: Fatty Acids in Industry (eds. R. W. Johnson, E. Fritz), Marcel Dekker, Inc., New York, 1989, p. 233]. Branched fatty acid derivatives may therefore be regarded as sought-after raw materials, for example for the lubricant or cosmetics industry. Where the derivatives are readily biodegradable, they could be used above all as "lost" lubricating oils.

On an industrial scale, branched fatty derivatives accumulate in particular in the Guerbet reaction in which fatty alcohols are dimerized at elevated temperatures in the presence of alkalis to form 2-alkyl-branched alcohols. Another method of producing branched fatty compounds is the dimerization of unsaturated fatty acids where complex mixtures of partly cyclic dimers are obtained in addition to methyl-branched monomer fatty acids. Finally, there is hydrocarboxylation or the Koch reaction in which 2,2-dimethyl-branched fatty compounds are obtained.

Towards the end of the eighties, Behr et al. produced internally alkyl-branched fatty acid derivatives by the rhodium-catalyzed addition of ethene onto linoleic or conjuene fatty acid esters using chloroform or n-hexane as solvent. A corresponding overview can be found in Fat Sci. Technol. 93, 20 (1991) and in EP 0 511 982 B1 (Henkel). The reaction is schematized below:

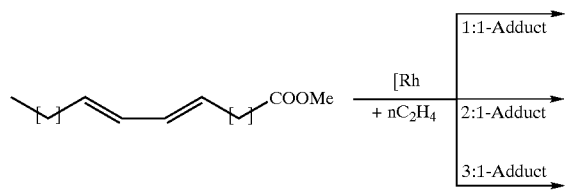

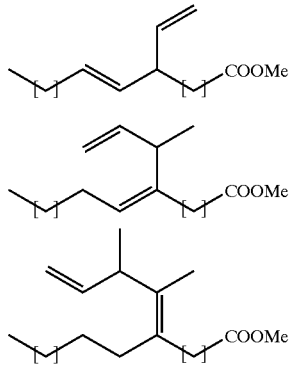

Besides single adducts, multiple adducts, i.e. adducts with a molar ratio of linoleic acid derivative to ethene of 1:1 to 1:3, are also consecutively formed at 80 to 100° C. and under pressures of 10 to 30 bar. Rhodium/olefin complexes and, above all, rhodium trichloride trihydrate are recommended as suitable catalysts. The homogeneous rhodium catalyst could not be re recycled without losses of activity.

EP 0 621 257 B1 (IFP) also describes a process for the production of double-branched fatty acid derivatives in which the oligomerization of linoleic acid methyl ester is carried out in chloroform as solvent in the presence of ionic rhodium complexes. EP 0 894 785 A1 and EP 0 976 715 A1 (IFP) both also relate to processes for the co-oligomerization of polyunsaturated fatty compounds with olefins in which nickel complexes are used together with ethyl aluminium chloride.

Although the yields obtained in known processes may be regarded as satisfactory, although still in need of improvement, industrial-scale operation has so far been unsuccessful because reliable, quantitative and industrially simple removal of the valuable, homogeneously dissolved transition metal catalyst from the reaction mixture has not yet been possible, especially since removal by distillation is unworkable on account of the high boiling points of the branched fatty compounds and the limited heat resistance of the catalysts.

Accordingly, the problem addressed by the present invention was to provide an improved process for the production of branched fatty compounds which would be distinguished from the prior art by simple, reliable and quantitative removal of the catalyst for at least equally high yields and selectivities.

DESCRIPTION OF THE INVENTION

The present invention relates to a process for the production of branched fatty compounds by co-oligomerization of unsaturated fatty compounds with α-olefins in the presence of homogeneous transition metal catalysts which is characterized in that the reaction is carried out in temperature controlled systems consisting of at least two solvents which are present as two phases at 20° C./1 bar and as a single phase at temperatures above 20° C.

The particular advantage of the process lies in the application of a new recycling concept for homogeneous transition metal catalysts by using temperature-controlled multicomponent solvent systems. The principle is based on the guarantee of simple phase separation and hence recycling of the catalyst by application of liquid/liquid two-phase technology at ambient temperature and on the fact that, at the same time, the reaction can be carried out in a single phase by suppressing the miscibility gap at the reaction temperature.

Unsaturated Fatty Compounds

Unsaturated fatty compounds which are suitable as starting materials for the oligomerization in the process according to the invention preferably correspond to formula (I):

$$R^1CO\text{—}OR^2 \qquad (I)$$

in which $R^1CO$ is an acyl group containing 12 to 22 carbon atoms and 1 to 3 double bonds and $R^2$ is hydrogen or a linear or branched alkyl group containing 1 to 4 carbon atoms. In addition, the unsaturated starting materials may also correspond to formula (II):

$$R^3\text{—}X \qquad (II)$$

in which $R^3$ is a hydrocarbon radical containing 12 to 22 carbon atoms and 1 to 3 double bonds and X is a hydroxyl or amino group. Typical examples are palmitoleic acid, oleic acid, elaidic acid, petroselic acid, ricinoleic acid, linoleic acid, linolenic acid, conjuene fatty acid and behenic acid and technical mixtures thereof and the corresponding alcohols or amines and the ethyl, propyl, isopropyl, butyl, isobutyl and, in particular, methyl esters of the acids mentioned. For example, the esters may also saturated components from their production providing they make up less than 50% by weight. Preferred starting materials are esters, acids, alcohols or amines corresponding to formula (I) or (II), in which $R^1CO$ is an acyl group and $R^3$ is a hydrocarbon radical containing 16 to 18 carbon atoms and two double bonds, more particularly so-called conjuene fatty acids or conjuene fatty acid esters or the corresponding alcohols or amines obtained by thermal isomerization of the double bonds of linoleic acid or linoleic acid derivatives into the conjuene position.

α-Olefins

α-Olefins suitable for use as a second reaction component in the process according to the invention preferably correspond to formula (III):

$$CH_2\text{=}CH\text{—}R^4 \qquad (III)$$

in which $R^4$ is hydrogen or an alkyl group containing 1 to 6 carbon atoms. Typical examples are butene, pentene and hexene. However, ethene, propene or mixtures thereof is/are normally used. The ratio of ester to olefin depends to a very large extent on the degree of substitution to be obtained in the branched fatty compounds. The quantity of ethene is normally adjusted through the ethene pressure in the reaction vessel, pressures of 10 to 50 and preferably 20 to 30 bar being typical.

Catalysts and Co-catalysts

The choice of the catalysts depends on whether they are suitable for liquid/liquid two-phase technology. The reaction normally takes place in the presence of homogeneously soluble, neutral or ionic rhodium and/or nickel catalysts such as, for example, $RhCl_3*3H_2O$, $[RhCl_4][PBu_4]$, $[RhCl(C_2H_4)_2]_2$, $[Rh(COD)Cl]_2$, $[Ni(MeCN)_6][BF_4]_2$ or $[Ni(MeCN)_6][AlCl_4]_2$. The use of $RhCl_3*3H_2O$, $[RhCl_4][PBu_4]$ and $[RhCl(C_2H_4)_2]_2$ is particularly preferred because yields of well above 50% of the theoretical can be obtained with them. By far the highest yields of up to 98% were obtained with rhodium trichloride trihydrate so that it is particularly preferred to use this catalyst which also shows poor solubility in nonpolar organic solvents.

By using suitable co-catalysts, yield and selectivity can be further improved. In particular, the use of the co-catalyst enables the catalyst to be recycled without significant losses of activity. The reaction may thus be carried out over very short reaction times (for example 2 h) and under mild conditions so that activity can be improved by a factor of up to 10. Suitable co-catalysts are, for example, acetyl chloride, acrylic acid chloride, allyl chloride, cinnamyl chloride, crotyl chloride, hexachloroacetone, cinnamic acid chloride or trichlorotoluene, cinnamyl chloride and cinnamic acid chloride being preferred. The molar ratio of catalyst to co-catalyst is typically between 1:1 and 1:200 and preferably between 1:10 and 1:25.

Temperature-controlled Solvent Systems

Solvents which have proved to be particularly suitable for liquid/liquid two-phase technology are, above all, alkylene glycols and/or alkylene carbonates containing 2 to 6 carbon atoms, more especially ethylene glycol, propylene glycol, propylene carbonate and mixtures thereof. However, multicomponent solvent systems which enable the reaction to be carried out in a single phase (suppression of the miscibility gap at relatively high temperatures) and which provide particularly effectively for simple phase separation at ambient temperature by two-phase technology have proved to be particularly advantageous.

In these new multicomponent solvent systems, a polar solvent component, such as an alkylene glycol or alkylene carbonate, is accompanied as co-solvents by at least one other, nonpolar solvent component, which forms a miscibility gap with the polar component for application of two-phase technology, and preferably by a third, medium-polarity solvent component by which the miscibility gap is closed at temperatures above ambient temperature, so that a homogeneous single-phase reaction system is present. The nonpolar co-solvents are typically selected from the group consisting of aliphatic and aromatic hydrocarbons (n-hexane, cyclohexane, heptane, petroleum ether or toluene). The medium-polarity co-solvents are typically selected from the group of ethers (methyl tert.butyl ether, 1,4-dioxane, tetrahydrofuran), aliphatic n-alcohols (methanol, ethanol, propanol, butanol) or aromatic hydrocarbons (anisole, toluene).

It has been found that particularly high yields are obtained above all in the presence of ethers and aliphatic hydrocarbons, such as cyclohexane, n-hexane or n-heptane. In addition, with 1,4-dioxane, the 2:1 adduct is obtained in high yields. Short-chain diols and alkylene carbonates are particularly suitable for catalyst recycling by virtue of their high polarity. Typical examples of mixed solvent systems are propylene carbonate/hexane (1:1), ethylene glycol/heptane (1:1) and, of new multicomponent solvent systems, propylene carbonate/hexane/methanol (1:1:1.6), propylene carbonate/heptane/toluene (1:1:2), propylene carbonate/hexane/toluene (1:1:2), ethylene glycol/heptane/THF (1:1:3), ethylene glycol/heptane/1,4-dioxane (1:1:3), propylene carbonate/heptane/anisole (1:1:1.5), propylene carbonate/heptane/THF (1.1:2), propylene carbonate/heptane/1,4-dioxane (1:1:1.5), propylene carbonate/heptane/toluene (1:1:2), ethylene glycol/heptane/butanol (1:1:1.2), ethylene glycol/toluene/1,4-dioxane (1:1:2.2), ethylene glycol/toluene/ethanol (1:1:0.75) or propylene carbonate/heptane/propanol (1:1:1.15). Ternary solvent mixtures of propylene carbonate/heptane or ethylene glycol/heptane and another co-solvent, which may be either an aromatic hydrocarbon, for example toluene or anisole, an aliphatic n-alcohol (methanol, ethanol, propanol, butanol) or an ether, for example THF, 1,4-dioxane or MTBE, are particularly preferred. The ratio by volume of solvent to co-solvent may typically be in the range from 1:1 to 1:4. Commensurate with the phase behavior, this ratio is quasi-infinitely variable as a function of, for example, the reaction temperature or the quantity of polar solvent used and infinitely many possible working points may be used.

Since long-chain fatty compounds show similar dissolving behavior to hydrocarbons, the starting materials may also serve as nonpolar co-solvents and replace the hydrocarbon component. The best results are obtained with mixtures where an ether, for example THF or 1,4-dioxane, or an aliphatic short-chain alcohol and the catalyst-containing solvent, preferably short-chain diols or alkylene carbonate, are present besides the fatty compound as an additional co-solvent. The volume/time yield can be considerably improved and the quantity of solvent reduced in this way. Accordingly, typical solvent systems are propylene carbonate/fatty ester/dioxane (1:1:0.4), propylene carbonate/fatty ester/dioxane (1:5.3:0.3) or propylene carbonate/fatty ester/ethanol (1:1:1.5). Instead of the fatty ester, conjuene fatty acid, for example, or the like may be directly used, for example in the propylene carbonate/conjuene fatty acid/1,4-dioxane (1:1:0.4) solvent system. Basically, however, the quantity of solvent or solvent mixture used is not critical and is determined solely by the quantity of substances to be solubilized.

Oligomerization

One particular embodiment of the invention is a process of the type mentioned at the beginning in which the unsaturated fatty compounds dissolved in a single phase are oligomerized with the olefins in the new multicomponent solvent systems described above at reaction temperatures above ambient temperature, the mixture is converted by cooling into a two-phase system in which one phase contains the branched fatty compounds and the other phase contains the homogeneously dissolved catalyst, the phases are separated and worked up. The oligomerization may be carried out in known manner. To this end, the fatty compounds are generally introduced into an autoclave together with the catalyst/co-catalyst in the solvent, the pressure reactor is heated to the reaction temperature of 50 to 100° C. and preferably 60 to 80° C. and the quantity of olefin required for the reaction is then introduced under pressure, a pressure of typically 10 to 50 bar and more particularly 20 to 30 bar being established. However, the reaction solution may also be saturated with ethene before the reaction temperature is reached, particularly when the formation of higher oligomers is to be prevented.

For successful catalyst recycling, the catalyst has to be completely recycled. Investigations of the phase composition of the reaction mixtures at ambient temperature have shown that the upper phase predominantly contains the branched fatty compounds and—depending on the multi-component solvent system selected—up to at most 20% by weight of solvent. The valuable-product phase may be further worked up by distillation, flash evaporation, extraction or a combination of these steps. The branched fatty compounds, which thereafter are obtained in substantially pure form, still contain double bonds. For certain applications, it may be necessary to harden the products. This may be done, for example, at 40 to 70° C. and under pressures of 10 to 30 bar in the presence of Pd/C catalysts and using methanol as solvent. The reaction times are normally of the order of 15 to 120 mins.

EXAMPLES

Example 1

9.3 g of a thermally conjugated and methyl-esterified sunflower oil fatty acids were introduced into a 300 ml stainless steel autoclave with a glass insert and disk stirrer together with 25 mg of rhodium trichloride trihydrate and 362 mg of cinnamyl chloride in 60 ml of a solvent mixture of propylene carbonate, heptane and toluene in a ratio by volume of 1:1:2. Ethene was then introduced under pressure in such a quantity that a pressure of 30 bar was established at a reaction temperature of 70° C. After a reaction time of 2 h, the reactor was cooled and vented. The organic valuable-product phase was separated by phase separation from the phase containing the dissolved catalyst. The two phases were then separately worked up. According to analysis by gas chromatography, a yield of ethene adducts of 95% of the theoretical, based on conjuene ester, was obtained. Analysis of the reaction products showed 55% of the 1:1 adduct and 40% of the 2:1 adduct.

Example 2

As in Example 1, 9.3 g of conjuene fatty acid methyl ester, 25 mg of rhodium trichloride trihydrate and 362 mg of cinnamyl chloride were introduced into a 66 ml stainless steel autoclave. 25 ml of a mixture of propylene carbonate, 1,4-dioxane and conjuene fatty acid methyl ester —which itself acted as solvent in this case—in a ratio by volume of 1:0.4:1 was used as the solvent. A yield of 90% of the theoretical was obtained, 61% of the 1:1 adduct and 29% of the 2:1 adduct being formed.

Example 3

As in Example 1, 13.1 g of conjuene fatty acid methyl ester were introduced into a 300 ml stainless steel autoclave with a glass insert and disk stirrer together with 36 mg of rhodium trichloride trihydrate and 515 mg of cinnamyl chloride. 70 ml of a mixture of ethylene glycol, 1,4-dioxane and conjuene fatty acid methyl ester—which itself acted as solvent in this case—in a ratio by volume of 1:1:2.8 was used as the solvent. A yield of 82% of the theoretical was obtained, 72% of the 1:1 adduct and 4% of the 2:1 adduct being formed.

Example 4

As in Example 1, 24.3 g of conjuene fatty acid methyl ester 66 mg of rhodium trichloride trihydrate and 953 mg of cinnamyl chloride were introduced into a 300 ml stainless steel autoclave with a glass insert and disk stirrer. 65 ml of a mixture of propylene carbonate, 1,4-dioxane and conjuene fatty acid methyl ester—which itself acted as solvent in this case—in a ratio by volume of 1:0.4:1 was used as the solvent. After 4 h, a yield of 98% of the theoretical was obtained, 25% of the 1:1 adduct and 73% of the 2:1 adduct being formed.

Example 5

Example 4 was repeated and the course of the co-oligomerization as a function of time was investigated. The results are set out in Table 1 below.

TABLE 1

Kinetics of the oligomerization of conjuene fatty acid methyl ester with ethene

| Reaction time [mins] | Total yield [% of theoretical] | Yield of 1:1 adduct [%] | Yield of 2:1 adduct [%] |
| --- | --- | --- | --- |
| 0 | 30 | 30 | 0 |
| 5 | 59 | 56 | 3 |
| 10 | 70 | 62 | 8 |
| 20 | 80 | 64 | 16 |

TABLE 1-continued

Kinetics of the oligomerization of conjuene fatty acid methyl ester with ethene

| Reaction time [mins] | Total yield [% of theoretical] | Yield of 1:1 adduct [%] | Yield of 2:1 adduct [%] |
|---|---|---|---|
| 40 | 91 | 59 | 32 |
| 60 | 93 | 47 | 44 |
| 93 | 95 | 38 | 57 |
| 121 | 96 | 31 | 65 |
| 180 | 97 | 25 | 72 |
| 240 | 97 | 22 | 75 |

Example 6

As in Example 1, 5.63 g of conjuene fatty acid methyl ester, 15.2 mg of rhodium trichloride trihydrate and 0.2395 g of cinnamic acid chloride were introduced into a 66 ml stainless steel autoclave. 7.54 g of propylene carbonate and 2.59 g of 1,4-dioxane were used as the solvent, the ratio by volume of propylene carbonate to 1,4-dioane to ester—which itself acted as solvent in this case—being 1:0.4:1. A yield of 72% of the theoretical was obtained, 52% of the 1:1 adduct and 20/ of the 2:1 adduct being formed.

Example 7

Conjuene fatty acid itself (thermally conjugated sunflower oil fatty acid) was used instead of the conjuene fatty acid methyl ester. The reaction was carried out as in Example 4. A yield of 88% of the theoretical was obtained, 51% of the 1:1 adduct and 37% of the 2:1 adduct being formed.

Example 8

As in Example 1, 75.85 g of conjuene fatty acid methyl ester 203.9 mg of rhodium trichloride trihydrate and 2.95 mg of cinnamyl chloride were introduced into a 300 ml stainless steel autoclave. 18.95 g of propylene carbonate were used as solvent, propylene carbonate and ester—which itself acted as solvent in this case—being mixed in a ratio by weight of 1:4 so that the reaction solution was a two-phase solution at room temperature and a single-phase solution at the reaction temperature. After 2 h, a yield of 93% of the theoretical was obtained, 44% of the 1:1 adduct and 49% of the 2:1 adduct being formed. After 5 h, the yield amounted to 97% of the theoretical, 27% of the 1:1 adduct and 70% of the 2:1 adduct being formed.

What is claimed is:

1. A process for the production of branched fatty compounds comprising reacting an unsaturated fatty compound and an α-olefin in the presence of a transition metal catalyst and a solvent mixture wherein the solvent mixture is a single liquid phase above 20° C. and is two liquid phases below 20° C.

2. The process of claim 1 wherein the unsaturated fatty compound is a compound of the formula (I):

$$R^1CO-OR^2 \qquad (I)$$

wherein $R^1CO$ is an acyl group having from 12 to 22 carbon atoms and from 1 to 3 double bonds and $R^2$ is hydrogen or a linear or branched alkyl group having from 1 to 4 carbon atoms.

3. The process of claim 1 wherein the unsaturated fatty compound is a compound of the formula (II):

$$R^3-X \qquad (II)$$

wherein $R^3$ is a hydrocarbon radical having from 12 to 22 carbon atoms and from 1 to 3 double bonds and X is a hydroxyl or amino group.

4. The process of claim 1 wherein the α-olefin is a compound of the formula (III):

$$CH_2=CH-R^4 \qquad (III)$$

wherein $R^4$ is hydrogen or an alkyl group containing 1 to 6 carbon atoms.

5. The process of claim 4 wherein the α-olefin is ethene, propene or a mixtures thereof.

6. The process of claim 1 wherein the catalyst is a rhodium and/or a nickel catalyst.

7. The process of claim 1 wherein the reaction is carried out in the presence of a co-catalyst selected from the group consisting of acetyl chloride, acrylic acid chloride, allyl chloride, cinnamyl chloride, crotyl chloride, hexachloroacetone, cinnamic acid chloride and trichlorotoluene.

8. The process of claim 1 wherein the solvent mixture is comprised of a polar and a nonpolar solvent having a sufficiently large miscibility gap.

9. The process of claim 8 wherein the polar solvent is selected from the group consisting of an alkylene glycol and an alkylene carbonate.

10. The process of claim 8 wherein the nonpolar solvent is selected from the group consisting of an aliphatic hydrocarbon, an aromatic hydrocarbon, an unsaturated fatty compound of the formula (I) or (II) and combinations thereof.

11. The process of claim 8 wherein the solvent mixture further comprises a medium-polarity solvent selected from the group consisting of an alcohol or an ether having from 1 to 6 carbon atoms and aromatic hydrocarbons containing 6 to 10 carbon atoms is additionally used.

12. The process of claim 1 wherein the solvent mixture is further comprised of a medium-polarity solvent selected from the group consisting of an alcohol or an ether having from 1 to 6 carbon atoms and an aromatic hydrocarbon having from 6 to 10 carbon atoms.

13. A process for the production of branched fatty compounds comprising the steps of: (1) reacting an unsaturated fatty compound and an α-olefin in the presence of a transition metal catalyst and a solvent mixture at a temperature above 20° C.; (2) cooling the solvent mixture from step (1) to form a first and second liquid phase system wherein the first phase comprises the branched fatty compounds and the second phase comprises the transition metal catalyst; (3) separating the first phase from the second phase.

* * * * *